(12) United States Patent
Higuchi et al.

(10) Patent No.: US 8,113,068 B2
(45) Date of Patent: Feb. 14, 2012

(54) MICRO-LIQUID TRANSFER APPARATUS AND MICRO-LIQUID TRANSFER METHOD

(75) Inventors: Akira Higuchi, Fukuoka (JP); Shirou Yamashita, Saga (JP); Kouji Shimogawa, Fukuoka (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 463 days.

(21) Appl. No.: 12/403,448

(22) Filed: Mar. 13, 2009

(65) Prior Publication Data
US 2009/0241699 A1 Oct. 1, 2009

(30) Foreign Application Priority Data
Mar. 14, 2008 (JP) .................................. 2008-065377

(51) Int. Cl.
*G01N 1/00* (2006.01)
(52) U.S. Cl. .................................................. 73/864.31
(58) Field of Classification Search ................ 73/864.31
See application file for complete search history.

(56) References Cited

U.S. PATENT DOCUMENTS

| | | | | |
|---|---|---|---|---|
| 3,568,735 A | * | 3/1971 | Lancaster | 141/238 |
| 7,429,258 B2 | * | 9/2008 | Angel et al. | 604/173 |
| 7,651,475 B2 | * | 1/2010 | Angel et al. | 604/65 |
| 2003/0083645 A1 | * | 5/2003 | Angel et al. | 604/890.1 |
| 2005/0228313 A1 | * | 10/2005 | Kaler et al. | 600/583 |
| 2007/0199923 A1 | * | 8/2007 | Takahashi | 216/88 |
| 2008/0138260 A1 | * | 6/2008 | Smith et al. | 422/208 |
| 2008/0213461 A1 | * | 9/2008 | Gill et al. | 427/2.3 |

FOREIGN PATENT DOCUMENTS

| | | |
|---|---|---|
| JP | 2003-329680 | 11/2003 |
| JP | 2004-518115 A | 6/2004 |
| JP | 2004-532983 A | 10/2004 |
| WO | 02-055199 A2 | 7/2002 |
| WO | 02-089984 A1 | 11/2002 |

* cited by examiner

*Primary Examiner* — Hezron E Williams
*Assistant Examiner* — Mark A Shabman
(74) *Attorney, Agent, or Firm* — Pearne & Gordon LLP

(57) ABSTRACT

In a micro-liquid transfer apparatus including two washing tanks (first washing tanks A and B), operations to transfer a sample are carried out using two pin tools (pin tools A and B) alternately. While one pin tool A is being mounted on a pin tool holder and is being used to transfer a liquid, the other pin tool B is waiting in a state where the lower end portions of their associated pins are immersed in the first washing tank B. While one pin tool A is being mounted on a pin tool holder and is being used to transfer a very small amount of liquid, the lower end portions of the respective pins of the other pin tool are washed, whereby the liquid transfer operations can be made in progress with no interruption and thus the generation of the operation waiting time can be prevented.

2 Claims, 3 Drawing Sheets

MICRO-LIQUID TRANSFER APPARATUS AND MICRO-LIQUID TRANSFER METHOD

BACKGROUND OF THE INVENTION

1. Field of the Invention

The present invention relates to apparatus and method for transferring a very small amount of liquid (micro-liquid) using a pin tool.

2. Description of the Related Art

In the field of biochemistry, there are carried out various kinds of analyses on a very small amount of sample held in the well of a micro plate. As a method for transferring a small amount of sample, there is generally known a method that uses multiple wells formed in a micro plate and a pin tool that is an aggregate of multiple pins respectively situated at positions corresponding to their associated wells. A specific groove working is executed in the leading ends of the respective pins. When such leading end portions of the pins are immersed in a sample that is stored in a container, a given amount of sample is attached to the respective pins due to the action of the surface tension. The sample attached to the pin leading end portion is contacted with the inner walls of the wells to transfer the sample thereto or to mix the sample with a liquid previously held in the wells, thereby transferring the sample. When the same pin tool is used to transfer another kind of sample, the pins must be immersed into a specific washing solution from the leading ends of the pins, the pins must be washed using ultrasonic waves and must be then rinsed using pure water, and the pins must be vacuum dried, thereby removing the attached substances from the pins completely (see the patent references 1 to 3).

Patent Reference 1: JP-A-2003-329680
Patent Reference 2: JP-A-2004-518115
Patent Reference 3: JP-A-2004-532983

Here, for the washing of the pins, there is necessary at least the time that includes about 30 seconds for the ultrasonic washing of the pins and about 10 seconds respectively for the rinsing and drying of the pins. This time provides a so-called operation waiting time while the sample transfer operation is interrupted because the pin tool is restricted by the washing operation. Therefore, when carrying out continuously the operations to transfer samples of different kinds, the operation waiting time is accumulated each time the sample to be handled is changed, resulting in the lowered productivity.

SUMMARY OF THE INVENTION

Thus, it is an object of the invention to provide apparatus and method for transferring a very small amount of liquid, which can wash pins without incurring the lowered productivity.

A micro-liquid transfer apparatus as defined in a first aspect of the invention includes a pin tool holder, alternately mounting thereon two pin tools including multiple pins each holding a micro-liquid attached to lower end portions of the pins, a work stage in which a container storing a sample and the transfer object are arranged, two washing tanks each storing a solvent for washing the lower end portions of the pins, a pin tool stocker supporting the pin tool separated from the pin tool holder such that the lower end portions of the pins of the pin tool separated from the pin tool holder are immersed in the solvent, and a pin tool transfer mechanism, moving the pin tool holder in a range including the work stage and two washing tanks, and carrying out an operation to transfer the attached sample to the transfer object by attaching the sample in the container to the lower ends of the pins at the work stage, wherein while one of the pin tools is being mounted on the pin tool holder so as to carry out the operation to transfer the micro-liquid, the lower end portions of the pins of the other pin tool stocked by the pin tool stocker in either of the washing tanks are washed.

A micro-liquid transfer method as defined in a second aspect of the invention is used in a micro-liquid transfer apparatus, which comprises a pin tool holder alternately mounting thereon two pin tools including multiple pins each holding a micro-liquid attached to lower end portions of the pins, a work stage in which a container storing a sample and the transfer object are arranged, two washing tanks, each storing a solvent for washing the lower end portions of the pins, a pin tool stocker supporting the pin tool separated from the pin tool holder such that the lower end portions of the pins of the pin tool separated from the pin tool holder are immersed in the solvent, and a pin tool transfer mechanism moving the pin tool holder in a range including the work stage and two washing tanks; the method comprising mounting one pin tool onto the pin tool holder by the pin tool transfer mechanism, and carrying out an operation to transfer the attached sample to a transfer object by attaching the sample in the container to the lower ends of the pins, and at the same time with the previous step, washing the lower end portions of the pins of the other pin tool that is stocked by the pin tool stocker in either of the washing tanks.

While the transfer operation is being executed using one of the two pin tools, the pins of the other pin tool are washed. Therefore, while replacing the pin tool that has ended the liquid transfer operation, the washed pin tool can be used immediately to carry out a next liquid transfer operation, which makes it possible to prevent a waiting time from being generated in the liquid transfer operation.

DESCRIPTION OF THE PREFERRED EMBODIMENTS

Figure 1:
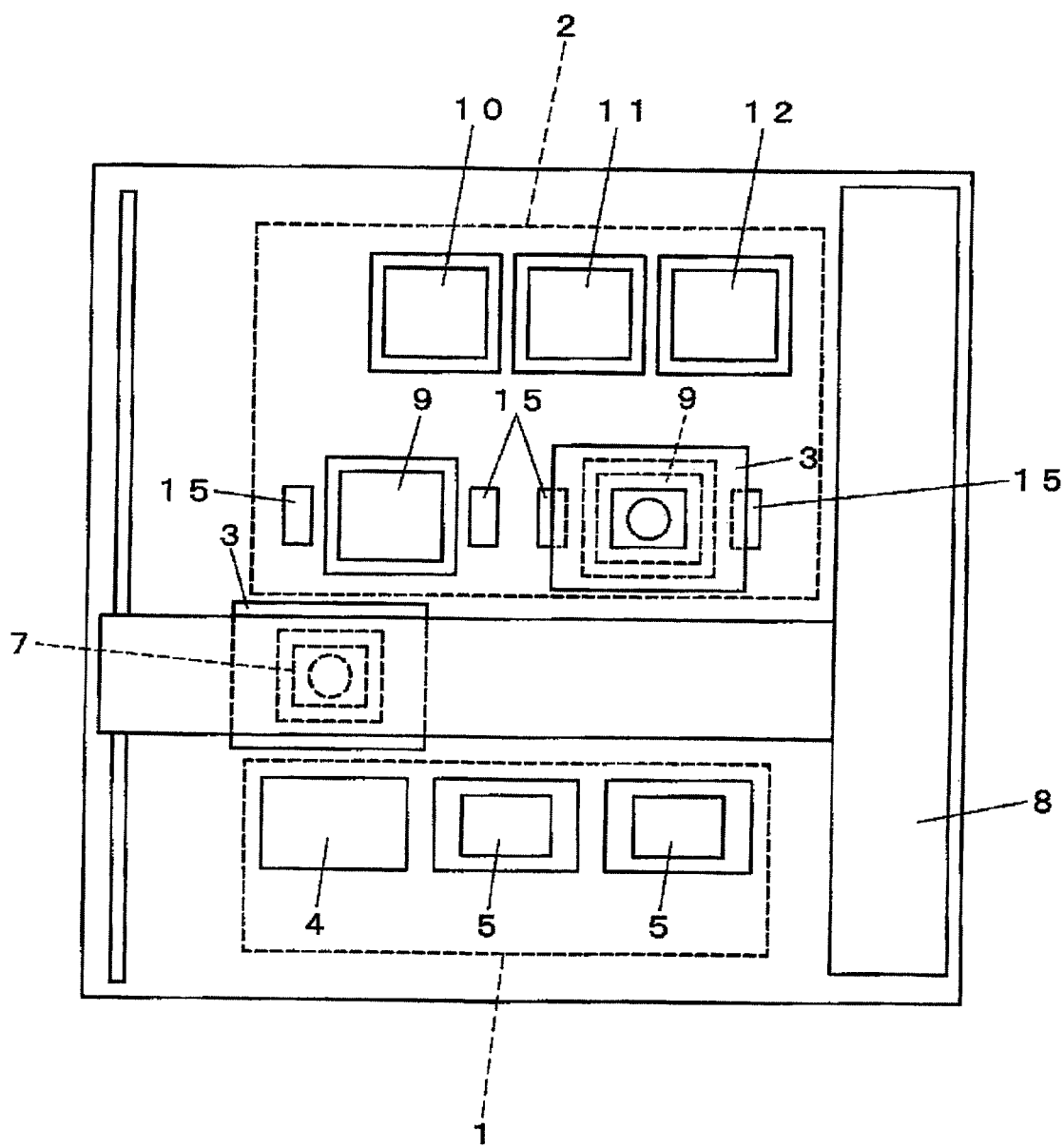
FIG. 1 is a plan view of a micro-liquid transfer apparatus according to an embodiment of the invention.
Figure 2:
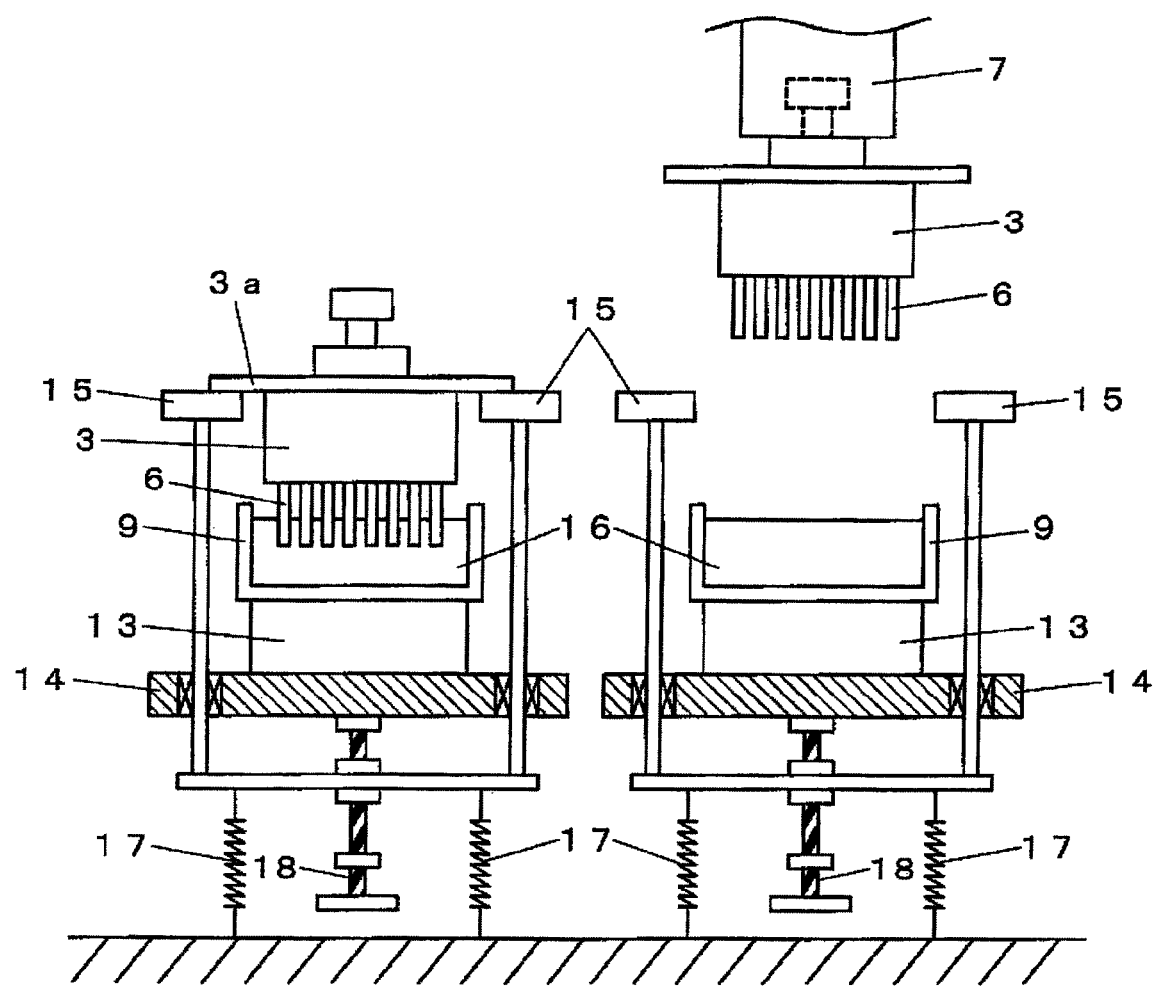
FIG. 2 is a side view of the micro-liquid transfer apparatus according to the embodiment of the invention.
Figure 3:
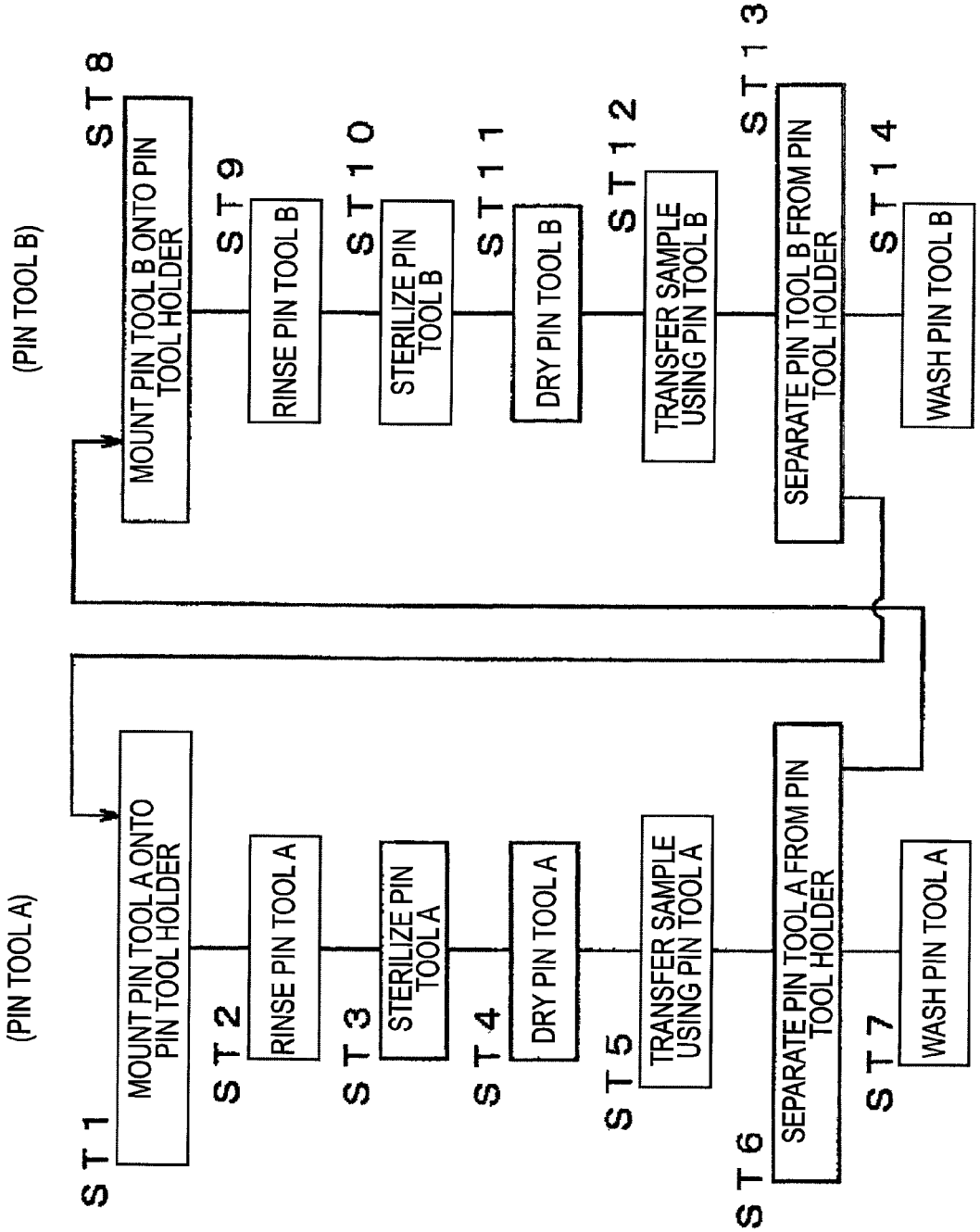
FIG. 3 is a flow chart of the operation of the micro-liquid transfer apparatus according to the embodiment of the invention.

Now, description will be given below of an embodiment of the invention with reference to the accompanying drawings. FIG. 1 is a plan view of a micro-liquid transfer apparatus according to an embodiment of the invention, FIG. 2 is a side view of the micro-liquid transfer apparatus according to the embodiment of the invention, and FIG. 3 is a flow chart of the operation of the micro-liquid transfer apparatus according to the embodiment of the invention.

The micro-liquid transfer apparatus includes a work stage 1 and a washing stage 2. The work stage 1 is a portion where a very small quantity of liquid is supplied using a pin tool 3; and, the work stage 1 includes a sample container 4 and two well plates 5 to which a sample is supplied. The washing stage 2 is a portion where a sample attached to the lower end portion of a pin 6 is washed. The pin 6 includes multiple pins respectively arranged so as to correspond to the positions of multiple wells respectively formed in the well plates 5, while the multiple pins 6 cooperate together in constituting the pin tool 3. In the lower end portions (leading end portions) of the respective pins 6, there are formed grooves that can facilitate the attaching of a very small amount of sample due to the surface tension thereof.

The micro-liquid transfer apparatus includes a pin tool transfer mechanism 8 which can move freely a pin tool holder 7 in the range including the work stage 1 and washing stage 2. The pin tool holder 7 can be moved up and down on the respective stages and is also be able to hold the pin tools 3 and remove such holding arbitrarily. In the sample transfer operation, the pin tool holder 7 holding the pin tool 3 thereon, when it is driven by the pin tool transfer mechanism 8, is moved to the work stage 1; and, the pin tool holder 7 firstly moves down the pin tool 3 toward the sample container 4, and then immerses the lower end portions of the respective pins 6 into a sample solution stored in the sample container 4 to attach a given amount of sample to the lower end portions of the pins 6. Next, the pin tool holder 7 moves down the pin tool 3 toward the well plates 5, and brings the sample attached to the lower end portions of the pins 6 into contact with the inner walls of the respective wells to transfer the sample to the wells inner walls or mixes the sample with a liquid already held by the wells, thereby transferring the sample to the well plates 5 to which the sample is to be supplied.

The washing stage 2 is a portion in which the lower end portions of the pins 6 can be washed; and, it includes two first washing tanks 9, a second washing tank 10, a third washing tank 11, and a drier 12. The two first washing tanks 9 are arranged side by side near to the work stage 1. The first washing tanks 9 are respectively put on their associated support bases 14 so that ultrasonic vibrations generated by their associated ultrasonic wave vibrators 13 can be transmitted. And, pin tool stockers 15 are used to support the flange portions 3a of the pin tools 3 in such a manner that the lower end portions of the respective pins 6 can be immersed in solvents 16 stored in the first washing tanks 9. In order to ease the impact that is generated when the pin tools 3 are put on the pin tool stockers 15, the pin tool stockers 15 are elastically supported by their associated springs 17 respectively. Since the distances between the flange portions 3a and the lower end portions of the pins 6 can vary depending on the kinds of the pins 6, each pin tool stocker 15 includes a height adjustment mechanism 18 which can fine adjust the height of the pin tool stocker 15.

The solvents, which are stored in the two first washing tanks 9, are respectively liquids which are used to facilitate the removal of the sample, dust or the like remaining attached to the lower end portions of the pins 6; and, as a typical example of such solvent, there is known DMSO (dimethyl sulfoxide). In each first washing tank 9, the residuals attached to the pins 6 can be removed due to the multiplier effect of a chemical action caused by the solvent and a physical action caused by the ultrasonic vibrations. The time necessary for washing in the first washing tank 9 is about 30 seconds.

In the second washing tank 10, there is stored pure water; and, the second washing tank 10 is used to rinse the pins 6 which have passed through the first washing tanks 9 and have the solvents left attached thereto. In the third washing tank 11, there is stored an alcohol-system solvent such as isopropanol; and, the third washing tank 11 sterilizes the pins 6 after rinsed. The drier 12 facilitates the evaporation of the sterilizing solvent attached to the pins 6 and finally finishes the washing of the pins 6. The operation times necessary in the second washing tank 10, third washing tank 11 and drier 12 are respectively about 10 seconds. Here, in the first washing tanks 9, the washing operation is carried out in a state where the pin tool 3 is separated from the pin tool holder 7; whereas, in the second washing tank 10, third washing tank 11 and drier 12, the washing operation is carried out in a state where the pin tool 3 is held on the pin tool holder 7.

Now, FIG. 3 is a flow chart of the operation of the micro-liquid transfer apparatus according to the embodiment of the invention. In the micro-liquid transfer apparatus including the above-mentioned two first washing tanks (that is, a first washing tank A and a first washing tank B), there is carried out an operation to transfer a sample using two pin tools (that is, a pin tool A and a pin tool B) alternately; and, while one pin tool A is mounted on the pin tool holder 7 to execute the liquid transfer operation, the other pin tool B is waiting for the next mounting thereof in such a state where the lower end portions of the pins 6 are immersed in the first washing tank B. Of course, at the then time, the other first washing tank A is not in use.

Firstly, description will be given of the flow of the operation in which the pin tool A is used for the sample transfer operation. That is, the pin tool A is mounted on the pin tool holder (ST1), is moved through a rinse step (ST2), a sterilizing step (ST3) and a drying step (ST4) to the work stage, and is then used to transfer the sample (ST5). On completion of the sample transfer operation, the pin tool A is separated from the pin tool holder (ST6) and is washed by the first washing tank A (ST7). The flow of the sample transfer operation, in which the pin tool B is used for the sample transfer operation, is also similar to the above. Specifically, the pin tool B, which is waiting in a state where the lower end portions of the pins 6 are immersed in the first washing tank B, is mounted on the pin tool holder from which the used pin tool A has been separated (ST8), is moved through a rinse step (ST9), a sterilizing step (ST10) and a drying step (ST11) to the work stage, and is then used to transfer the sample (ST12). On completion of the sample transfer operation, the pin tool B is separated from the pin tool holder (ST13), and is washed by the first washing tank B (ST14).

While the sample transfer operation is being carried out using the pin tool B, the pin tool A is washed sufficiently in the first washing tank A. Therefore, the pin tool A is held in a state where it can be mounted immediately onto the pin tool holder to carry out the next sample transfer operation.

As described above, according to the micro-liquid transfer apparatus and method of the invention, while one pin tool is mounted on a pin tool holder and is used to transfer a very small amount of liquid, the lower end portions of the pins included in the other pin tool are washed, whereby the liquid transfer operation can be executed smoothly with no interruption and thus the generation of the operation waiting time can be prevented.

The invention is especially useful in a field where a very small amount of liquid is supplied using a pin tool, from the viewpoint of enhancement in the production efficiency.

What is claimed is:

1. A micro-liquid transfer apparatus for transferring a micro-liquid to a transfer object, the micro-liquid transfer apparatus comprising:

a pin tool holder for alternately mounting thereon two pin tools including multiple pins each holding a micro-liquid attached to lower end portions of the pins;

a work stage, in which a container storing a sample and the transfer object are arranged;

two washing tanks, each storing a solvent for washing the lower end portions of the pins;

a pin tool stocker for supporting one of the pin tools separated from the pin tool holder such that the lower end portions of the pins of the separated pin tool are immersed in the solvent when the separated pin tool is supported by the pin tool stocker; and a pin tool transfer mechanism for moving the pin tool holder in a range including the work stage and two washing tanks, and capable of carrying out an operation to transfer the attached sample to the transfer object by attaching the sample in the container to the lower ends of the pins at the work stage;

wherein while one of the pin tools is mounted on the pin tool holder to carry out the operation to transfer the micro-liquid, the lower end portions of the pins of the other pin tool stocked by the pin tool stocker in either of the washing tanks are washed.

2. A micro-liquid transfer method for use in a micro-liquid transfer apparatus, in which the micro-liquid transfer apparatus comprises, a pin tool holder alternately mounting thereon two pin tools including multiple pins each holding a micro-liquid attached to lower end portions of the pins, a work stage in which a container storing a sample and the transfer object are arranged, two washing tanks, each storing a solvent for washing the lower end portions of the pins, a pin tool stocker supporting the pin tool separated from the pin tool holder such that the lower end portions of the pins of the pin tool separated from the pin tool holder are immersed in the solvent, and a pin tool transfer mechanism for moving the pin tool holder in a range including the work stage and two washing tanks; the method comprising:

mounting one pin tool onto the pin tool holder by the pin tool transfer mechanism, attaching the sample in the container to the lower ends of the pins, and carrying out an operation to transfer the attached sample to a transfer object; and at the same time with the previous step, washing the lower end portions of the pins of the other pin tool that is stocked by the pin tool stocker in either of the washing tanks.

* * * * *